United States Patent [19]

Jones et al.

[11] 4,082,666
[45] Apr. 4, 1978

[54] END POINT QUALITY CONTROL LIGHT CIRCUIT

[75] Inventors: Charles L. Jones; Dominic Aradio, both of El Paso, Tex.

[73] Assignee: Continental Water Conditioning Corporation, El Paso, Tex.

[21] Appl. No.: 716,150

[22] Filed: Aug. 20, 1976

[51] Int. Cl.² .............................................. C02B 1/76
[52] U.S. Cl. ................................... 210/93; 210/96 R; 340/236; 137/93
[58] Field of Search ..................... 210/93, 94; 340/236, 340/244; 137/93

[56] References Cited

U.S. PATENT DOCUMENTS

| | | | |
|---|---|---|---|
| 3,334,745 | 8/1967 | Burgess et al. | 210/93 |
| 3,343,045 | 4/1967 | Law et al. | 137/93 |
| 3,410,292 | 11/1968 | Bennett et al. | 210/96 X |
| 3,430,129 | 2/1969 | Cardeiro | 137/93 X |
| 3,652,910 | 3/1972 | Urbain | 210/96 X |
| 3,680,070 | 7/1972 | Nystuen | 340/244 |
| 3,768,649 | 10/1973 | Fleckenstein | 210/96 |
| 3,796,925 | 3/1974 | Breeming | 137/93 |
| 3,932,279 | 1/1976 | Yocum | 210/96 R |

OTHER PUBLICATIONS

Beckman Instruments Inc., "Water Purity Controller," Instruction Manual, 18 pp.
Devon Products, Inc., "Conductivity Indicators for Home and Office," 4 pp., June 30, 1976.

*Primary Examiner*—John Adee
*Attorney, Agent, or Firm*—Fleit & Jacobson

[57] ABSTRACT

An end point quality control light circuit for a water demineralizer. The quality control light circuit comprises a power cord, a housing for the electronics, and a probe-light assembly. The probe-light assembly includes a pair of spaced apart A.C. energized probes, and applies approximately 12 volts to the water. The probes are transformer isolated from the power input, and the final drive to an indicating lamp is transistorized. The current through the probes, directly proportional to the quality of the water, develops a voltage that is compared to a threshold voltage. The indicating lamp is illuminated to indicate high water quality, and is switched off by the final drive transistor when the water quality becomes unacceptable. An optional switching circuit, isolated from the quality control circuit, enables the actuation or control of external devices in dependence upon water quality. Various techniques for minimizing leakage currents are also disclosed.

32 Claims, 5 Drawing Figures

END POINT QUALITY CONTROL LIGHT CIRCUIT

BACKGROUND OF THE INVENTION

The present invention relates to an end point quality control light circuit designed for specific use with a water purifier, or demineralizer, unit. Yet the inventive circuit finds application wherever the quality of an effluent is important.

A demineralizer unit is disclosed in U.S. Pat. No. 3,245,537; this unit includes an integral end point quality control light. An improved, screw-in end point quality control light unit can be seen in U.S. Pat. No. 3,334,745. Each of these patents is owned by the present assignee. In the latter of these known end point lights, a neon bulb, two resistors, a pair of probes, and power wires for bringing standard household current to the bulb and probes are encapsulated in a common housing. The housing is externally threaded to enable association with mating threads of the demineralizer unit's discharge spout. The probes reside in the discharge path of the water, and are excited by approximately 60 volts A.C.; water quality is indicated by the state of the neon bulb.

This known end point quality control device is quite effective. However, recently enacted and expected codes, setting stringent requirements for electrical and electronic measuring and control instrumentation, indicate the possible need for redesign of such a device. As an example, the attention of the reader is directed to the American National Standard, Safety Requirements for Electrical and Electronic Measuring and Controlling Instrumentation (the ANSI Code), ANSI C39.5-1974. This code specifies safety requirements for devices such as end point quality control lights, and sets maximum permissible limits for electrical parameters such as insulation breakdown (2500v.) and leakage current (0.5ma). In this latter regard, a code enacted by the city of Los Angeles limits leakage current to 0.005ma for medical devices.

It is toward the development of an end point quality control light circuit capable of meeting the most stringent codes, that the present invention is directed.

SUMMARY OF THE INVENTION

The present invention relates to an end point quality control light circuit that is powered by standard household current, that includes a pair of probes isolated from the source of power, and that applies only on the order of 12 volts to the water being monitored. The quality of the water is indicated by a high luminosity incandescent lamp switched by means of a sharp turn-off integrated circuit. The electronic circuit associating with the probe-light unit is totally enclosed, is transformer-isolated from the power source, and has extremely low leakage current and a high insulation breakdown point. An optional feature of the inventive device is a totally isolated switching circuit which follows the operation of the indicator light and which provides switching capabilities for external loads up to on the order of 4 amperes.

Accordingly, it is the main object of the present invention to provide an end point quality control light for a demineralizer unit which is capable of meeting the most stringent electrical codes.

A more specific object of the present invention is to provide an end point quality control light whose major components are isolated from the source of electrical power.

Yet another object of the present invention is to provide an end point quality control light which applies a low voltage to the liquid being monitored.

A further object of the present invention is to provide an end point quality control light circuit having exceedingly low leakage currents and an exceedingly high insulation breakdown point.

Still another object of the present invention is to provide an end point quality control light having an indicating lamp of extremely high luminosity.

A further object of the present invention is to provide an end point quality control light which responds quickly and accurately to the quality of the liquid being monitored.

Another object of the present invention is to provide an end point quality control light having switching capabilities for external loads.

Yet a further object of the present invention is to provide an improved circuit for monitoring the quality of an effluent.

Still another object of the present invention is to provide a circuit, for monitoring the quality of an effluent, and for controlling external devices in dependence upon the quality of the effluent being monitored.

The foregoing and other objects of the present invention, as well as many of the attendant advantages thereof, will become more readily apparent when reference is made to the following description, taken in conjunction with the accompanying drawings.

DETAILED DESCRIPTION OF THE DRAWINGS

Figure 1:
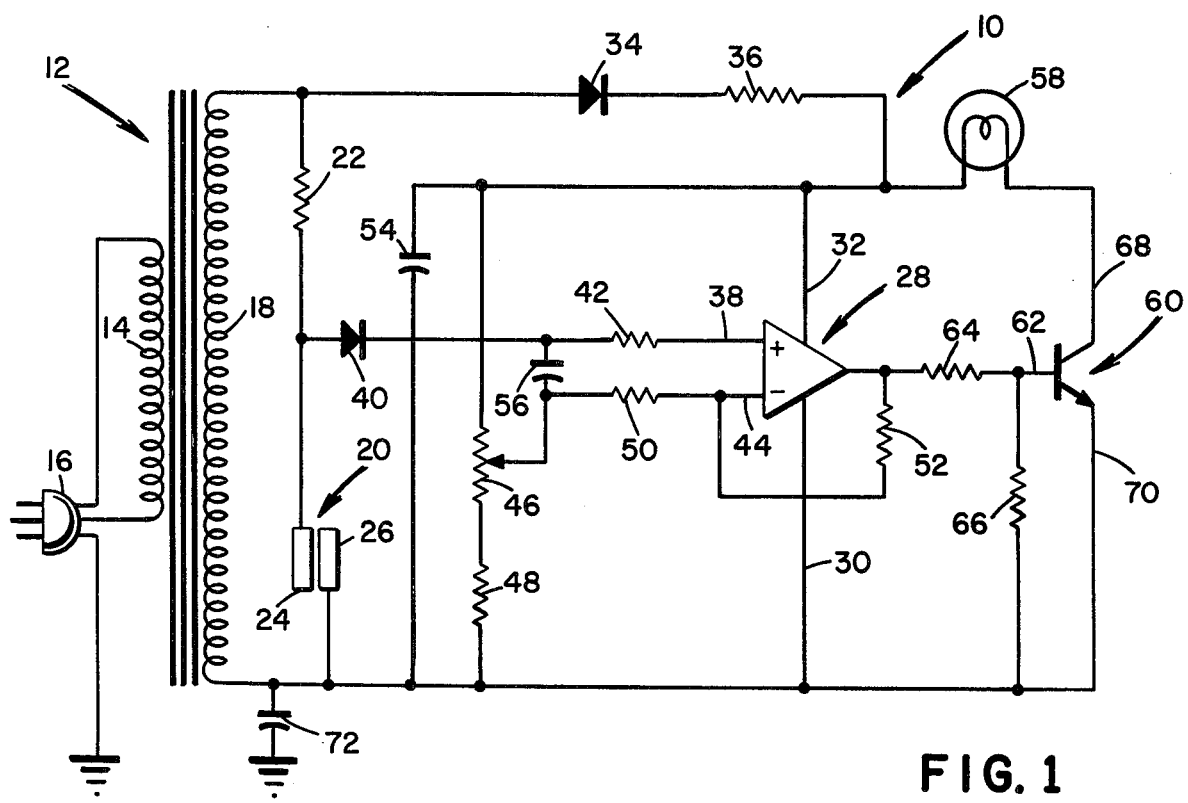
FIG. 1 is a circuit schematic illustrating the end point quality control light forming a part of the present invention.

With reference first to FIG. 1, the configuration of the inventive end point quality control light circuit will be described, in the environment of a water demineralizer unit. The inventive circuit is shown generally at 10, and receives standard household 110–120v A.C. energization through a transformer 12, the primary winding 14 of which associates with a grounded male plug 16. Transformer 12 is of the type which has a high insulation breakdown point; one such transformer is manufactured by Signal Transformer Co., Inc. of Brooklyn, New York under Size 5, 12VA, Part No. 241-5-24. The secondary winding of transformer 12 is denoted 18, and develops on the order of 25 volts from the input voltage across primary winding 14. In series with the secondary winding 18 of transformer 12, is a probe 20 and a dropping resistor 22, probe 20 taking the form of two conductive probe elements 24 and 26, adapted to reside within the water whose quality is being monitored.

An operational amplifier 28 is a major component of the inventive circuit 10, and receives the necessary operating bias from power lines 30 and 32. Line 30 is connected directly to one side of the secondary winding 18, while line 32 is connected to the opposite side of winding 18, through a voltage supply and rectifying diode 34, and a voltage dropping resistor 36.

The current flow between probe elements 24 and 26 is converted to a voltage and is sensed at the non-inverting input 38 of operational amplifier 28 through a rectifying diode 40 and an input resistor 42. This voltage is compared with a fixed reference voltage appearing at the inverting input 44 of operational amplifier 28, the magnitude of the fixed reference voltage being determined by a voltage divider network including a potentiometer 46, a voltage divider resistor 48 and an input resistor 50. Input resistor 50 and a positive feedback resistor 52 determine the gain of the operational amplifier 28. For example, if feedback resistor 52 is ten times the value of resistor 50, then the gain of amplifier 28 is 10. A filtering capacitor 54 is connected across the power supply lines of the operational amplifier 28, and serves to smooth the output of the supply voltage rectifier 34. The amplifier 28 is made to see a more constant impedance by the operation of an impedance matching capacitor 56 connected across the input leads 38 and 44 of the operational amplifier 28.

An incandescent quality light 58 (24v rating) and an NPN transistor 60 complete a series circuit with the secondary winding 18 of transformer 12. And as can be seen, current is permitted to flow through quality light 58 when transistor 60 is in its conductive state, but is interrupted when transistor 60 is non-conductive. In this regard, the base 62 of transistor 60 is biased by a voltage divider network including resistors 64 and 66. The collector 68 of transistor 60 is connected directly to the quality light 58, while the emitter 70 feeds to one side of the secondary winding 18 of transformer 12.

A bypass capacitor 72 is connected between ground and the secondary winding 18 of transformer 12. The function of capacitor 72 is to bypass any leakage current across transformer 12 to ground, and it is this capacitor which enhances the leakage current properties of the inventive circuit. Capacitor 72 is, in particular, a polarized electrolytic of the tantalum wet anode variety such as is sold by Cornell-Dubilier as Type TX65B; the value of capacitor is between 10 and 160 mfd, and is more preferably between 25 and 47 mfd.

With continuing reference to FIG. 1, the operation of the inventive quality control light circuit will be described. Conductive elements 24 and 26 of probe 20, A.C. energized by secondary winding 18, are submerged in the water being monitored. When the water is pure, it exhibits a high impedance, and very little current flows between elements 24 and 26. Accordingly, a high voltage appears at the non-inverting input 38 of operational amplifier 28. The fixed reference voltage that is impressed upon the inverting input 44 is of a value less than this high voltage on the non-inverting input 38, and hence operational amplifier 28 issues an output which biases transistor 60 into its conductive state. When transistor 60 conducts, current flows through the quality light 58, and the light is illuminated. The illuminated condition of light 58 indicates high quality water.

As the quality of the water deteriorates, the conductivity of the water increases. Accordingly, more and more current passes across the probe elements 24 and 26. The voltage on conductive element 24 therefore moves toward that potential of conductive element 26, and hence the voltage on the non-inverting input 38 of operational amplifier 28 decreases. Potentiometer 46, used to set the value of the reference voltage at input 44, is preadjusted to a value so that the reference voltage equals the voltage on input 38 just when the quality of the water becomes unacceptable. As soon as the water quality becomes unacceptable, therefore, the voltage on non-inverting input 38 drops to a value less than the fixed reference voltage on inverting input 44. At this instant, operational amplifier 28 switches over, and the bias to transistor 60 is removed. Accordingly, transistor 60 reverts to its non-conductive state, and blocks the flow of current to the quality light 58. Quality light 58 therefore turns off, indicating an unacceptable quality of water.

Figure 2:
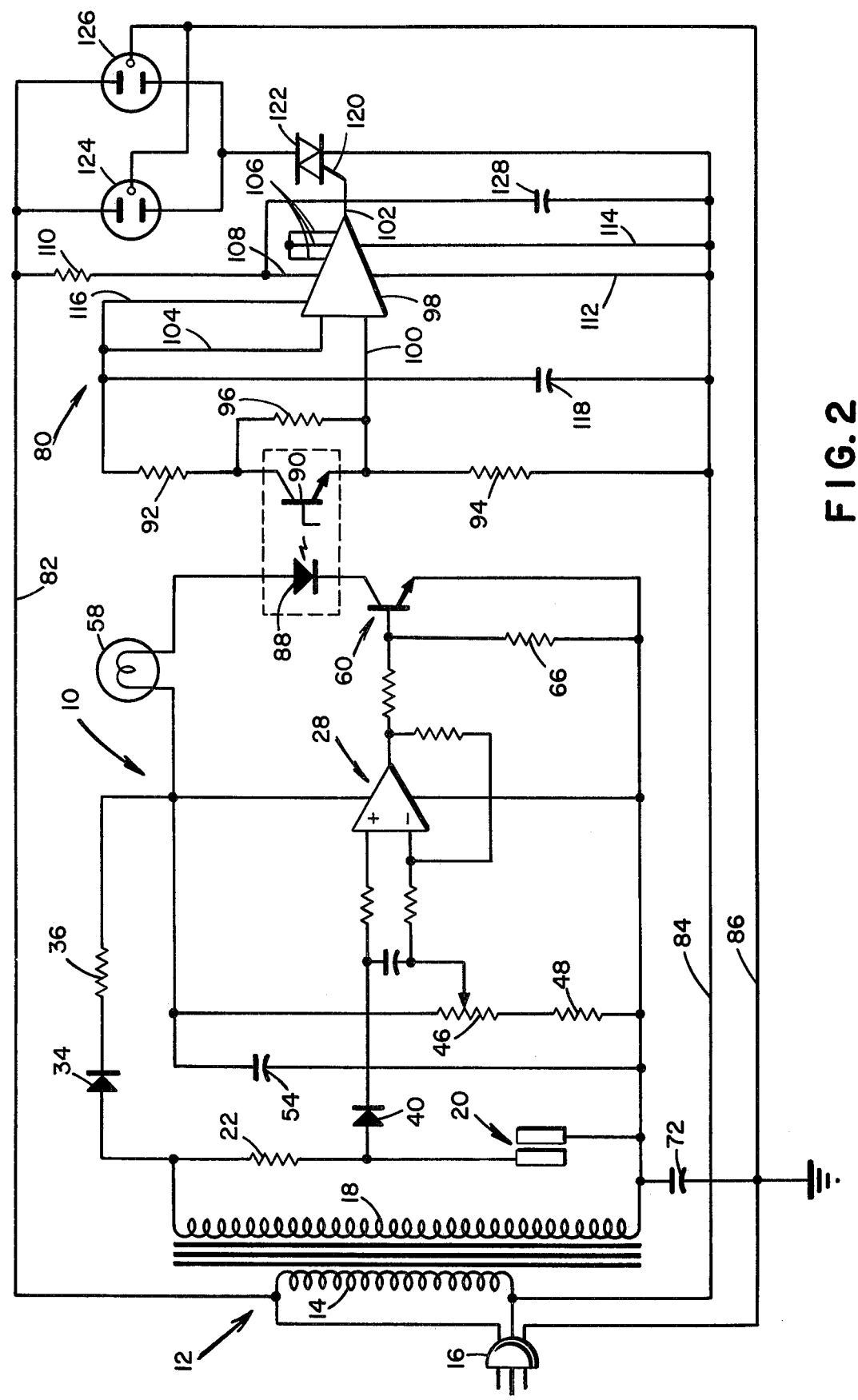
FIG. 2 is a circuit schematic of the end point quality control light in combination with an optional output switching circuit.

With reference now to FIG. 2, the optional remote switching feature will be described. This switching option is shown generally at 80, following the end point quality control circuit 10 already described when reference was made to FIG. 1.

The switching circuit 80 derives power from standard household 110–120v A.C., is completely isolated from circuit 10, and is actuated as a result of current flow through a light emitting diode 88 in series with the quality light 58 of circuit 10. Power is delivered to switching circuit 80 from primary winding 14, through the means of power supply lines 82 and 84, and a ground conductor 86 originates from the ground pin of male plug 16. With the exception that the light emitting diode 88 is series connected to the quality light 58, the end point quality control circuit 10 shown in FIG. 2 is identical to that shown in FIG. 1. Accordingly, common reference numbers are utilized.

Associating with light emitting diode 88 is a phototransistor 90. Voltage dividing resistors 92 and 94 are connected, respectively, to the collector and emitter sides of phototransistor 90, and a bypass resistor 96 is shunted across the collector and emitter.

A zero voltage switch 98 is the central element of the remote switching circuit 80. When the input terminal 100 of zero voltage switch 98 experiences a voltage in excess of a predetermined threshold, then output pulses are issued at output line 102. This threshold is internally set by a comparator circuit, the wiring for which is indicated at shorted terminals 106. Phototransistor 90 is D.C. biased from a D.C. output lead 104 of the zero voltage switch.

The zero voltage switch 98 derives its power from a lead 108 connected to power supply line 82 through a voltage dropping resistor 110, and a lead 112 connected to power supply line 84. The zero voltage switch 98 has a return line 114 associating with the internal voltage divider determining the threshold, and a feedback line 116 which biases the output stage of the switch so that output current capability is increased. In addition, a filtering capacitor 118 is utilized to smooth the D.C. output appearing at lead 104.

The output line 102 of the zero voltage switch 98 is connected to the gate 120 of a triac 122, the annodes of which are in series with the power lines 82 and 84 and load receptacles shown at 124 and 126. Therefore, when triac 122 is conductive, the load receptacles 124 and 126 are energized. A capacitor 128 associates with the supply line to zero voltage switch 98, and serves to internally widen the output pulses of the switch so that the triac 122 has sufficient time to reach holding current.

The operation of the remote switching option will now be described. It is sometimes desirable to operate external devices, such as lights, motors, alarms, and the like, during the time when water quality is acceptable, and to automatically deactuate such external devices when the water quality drops. The remote switching option 80 provides such capabilities when external devices are plugged into the load receptacles 124 and 126. The switching option may also be utilized to control down-stream equipment such as water pumps, or could actuate a double-pole relay to switch from one water treatment leg to another. And the quality light 58 can be used with or without the switching option 80 in the circuit.

It will be recalled that when the water quality is acceptable, current flows through the circuit including the quality light 58 and the transistor 60. With current flowing, the light emitting diode 88 is energized and issues a light signal that is received by the electrically isolated phototransistor 90. Phototransistor 90 then becomes conductive, shorting the bypass resistor 96 out of the circuit. This results in the emitter of phototransistor 90 going high (to on the order of 4.3v). Upon the emitter of phototransistor 90 going high and exceeding the threshold voltage of the zero voltage switch 98 (on the order of 3.1v), the switch 98 begins to issue a pulsating signal at its output 102. A pulse is developed each time the A.C. supply voltage crosses zero. The signal at output 102 gates the triac 122 conductive, and hence closes the series circuit connection of load receptacles 124 and 126. Accordingly, the external devices connected to the load receptacles 124 and 126 are energized.

When the quality of the water falls below the acceptable threshold, on the other hand, operational amplifier 28 switches over, transistor 60 becomes non-conductive, and hence light emitting diode 88 is turned off. Phototransistor 90 therefore also becomes non-conductive, and shunt resistor 96 returns to the circuit. At this occurrence, the voltage on the emitter of the photoresistor 90 drops, bringing with it, the input to the zero voltage switch 98 appearing at lead 100. The voltage on lead 100 will then drop below the internal threshold value of the zero voltage switch 98, and hence the switch will turn off. Accordingly, triac 122 becomes non-conductive, opening the series circuit including the load receptacles 124 and 126, and deactuating or switching whatever external devices are connected to the receptacles.

Figure 3:
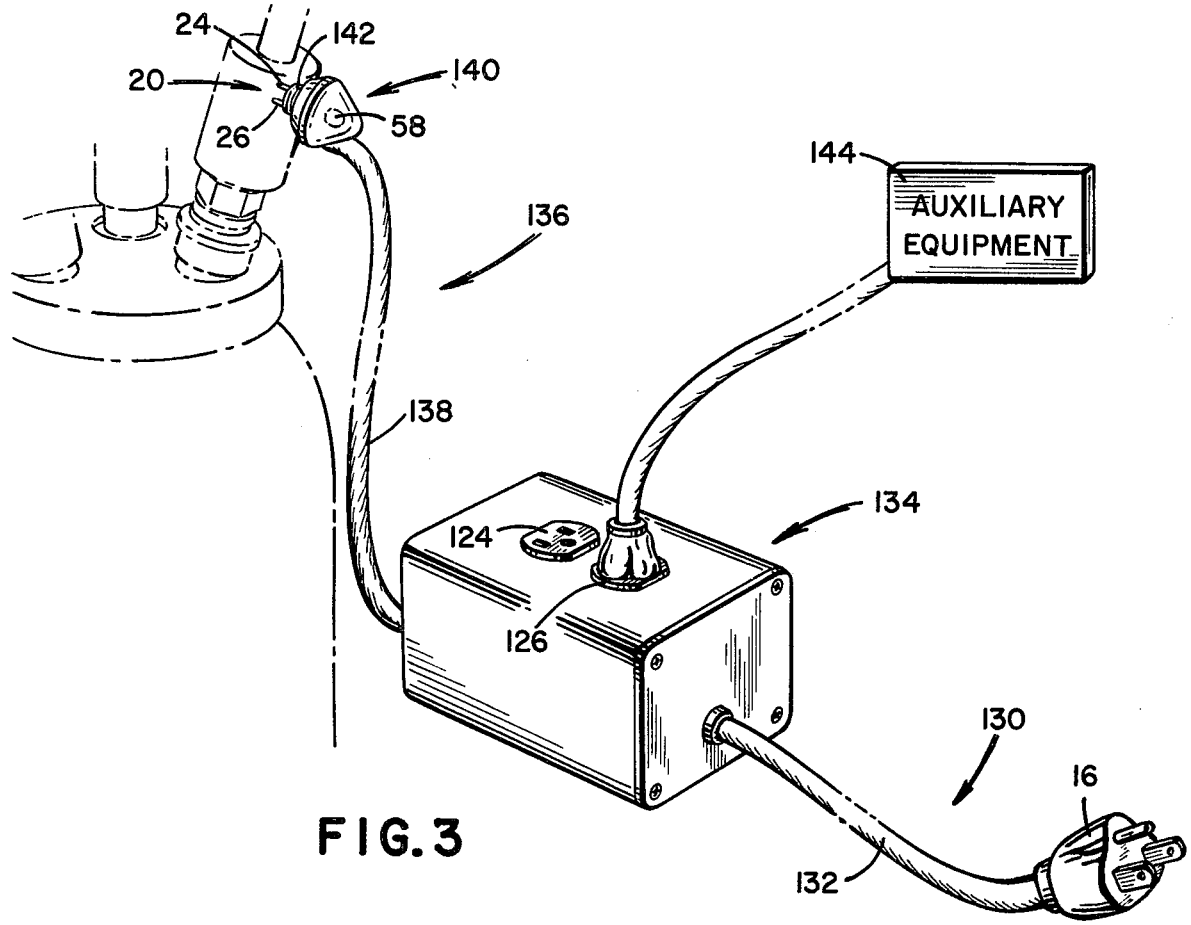
FIG. 3 is a perspective drawing showing the inventive end point quality control light mounted on a demineralizer unit and associated with auxiliary equipment through its optional switching circuit.

FIG. 3 illustrates the overall configuration of the inventive device. As can be seen, the device includes three basic components. The first is a power cord shown generally at 130, and including the male plug 16 already described. A three-conductor cord 132 extends from plug 16 and enters the second basic component, a housing shown generally at 134. Cord 132 is strain relieved. Housing 134 supports the two load receptacles 124 and 126, and encases all of the electronic circuitry.

The third basic component is a probe-light assembly shown generally at 136. A four-conductor cord 138, also strain relieved, emerges from the housing 134 and terminates in a probe casing 140 which encapsulates the quality light 58, and from which extends the conductive elements 24 and 26 of the probe 20. Casing 140 is of a transparent plastic material. The base of casing 140 is threaded, as shown at 142, to be received in the discharge spout of the demineralizer unit. The outline of a demineralizer unit is shown in phantom, but can be seen in detail by referring to U.S. Pat. No. 3,334,745 mentioned above. A plug from a piece of auxiliary equipment 144 associates with receptable 126.

Figure 4:
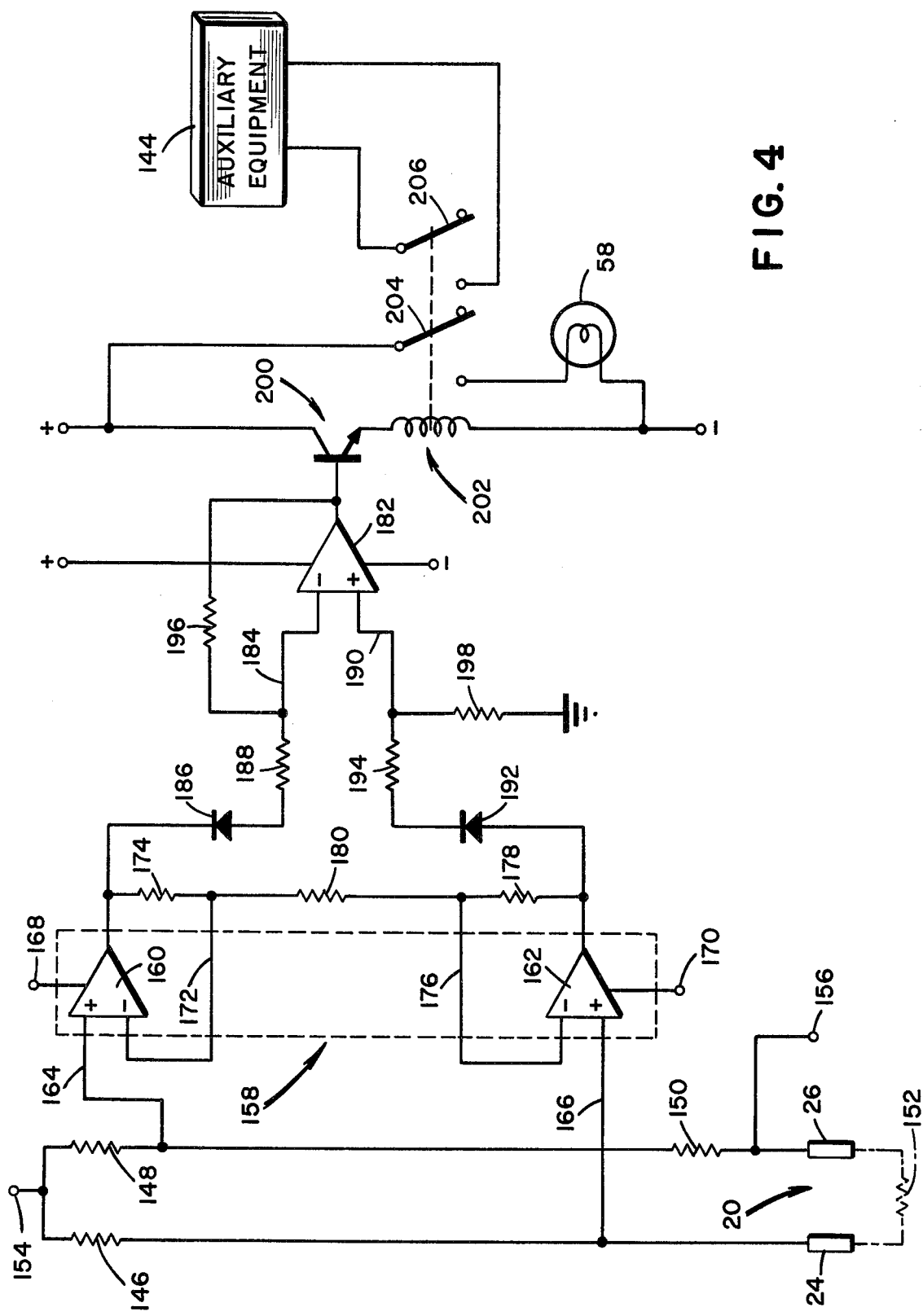
FIG. 4 is a schematic of another circuit for minimizing leakage currents.

With reference now to FIG. 4, a first alternate circuit for minimizing leakage currents will be described. As in the circuits of FIGS. 1 and 2, a probe 20 in the form of two conductive probe elements 24 and 26 is adapted to reside within the liquid being monitored. In FIG. 4, probe elements 24 and 26 are part of a resistive bridge circuit, the remaining elements of which are resistors 146, 148 and 150, and the inherent and varying resistance between probe elements 24 and 26, shown in phantom at 152. The bridge circuit is excited by a 24v A.C. source at terminals 154 and 156.

The second stage of the circuit illustrated in FIG. 4 is an isolation stage 158 comprising a pair of amplifiers 160 and 162 connected in unity, or buffer, configuration. Input 164 of amplifier 160 senses a threshold voltage set by resistors 148 and 150, and the 24 volt excitation source. The input 166 of amplifier 162, on the other hand, senses a variable voltage proportional to the conductivity of the liquid being monitored and dependent upon the inherent resistance (152) of the liquid. Amplifiers 160, 162, and 182 receive +12 volts power supply voltage at terminal 168 and −12 volts power supply voltage at terminal 170. The second input of amplifier 160 is part of a feedback circuit including line 172 and resistor 174. Amplifier 162 has a similar feedback path comprising line 176 and resistor 178. A resistor 180 couples the respective outputs of amplifiers 160 and 162.

A comparator 182 receives input from the respective isolation amplifiers 160 and 162. The output of amplifier 160 is fed to a first input 184 of comparator 182 through a diode 186 and a resistor 188. The output of amplifier 162 is delivered to the other input 190 of comparator 182 through a diode 192 and a resistor 194. A resistor 196 provides feedback for comparator 182, while resistor 198 connects input 190 to ground.

The output of comparator 182 is fed to the gate of a transistor 200, the collector of which is biased by +12 volts, and the emitter of which associates with −12 volt bias and the coil of a control relay 202. Relay 202 controls the operation of contacts 204 which opens and closes a series circuit including incandescent quality light 58. As illustrated in FIG. 4, relay 202 optionally controls contacts 206 for operating auxiliary equipment 144.

The operation of the circuit illustrated in FIG. 4 is as follows. When the quality of the liquid being monitored is acceptable, comparator 182 issues an output which actuates relay 202 and closes the respective circuits of quality light 58 and the auxiliary equipment 144. When the quality becomes unacceptable, on the other hand, the conductivity of the liquid increases, representing a decrease in the value of resistor 152. Accordingly, the voltage appearing at input 166 of amplifier 162 would drop below the threshold voltage impressed at the input 164 of amplifier 160. The output of amplifier 160 appearing at input 184 of comparator 182 therefore goes above the output of amplifier 162, in turn, impressed at terminal 190 of comparator 182. Comparator 182 therefore turns off, releasing relay 202, opening contacts 204, and hence turning quality light 58 off. At the same time, relay actuated contacts 206 would open, and the operation of the auxiliary equipment indicated at 144 would switch over.

The circuit illustrated in FIG. 4 serves well to minimize leakage currents, without the use of the transformer 12 illustrated in FIGS. 1 and 2. Amplifiers 160 and 162 are in buffer configuration, exhibit exceedingly high input impedance, and are virtually insensitive to changes in current. Because of this configuration, the input terminals of amplifiers 160 and 162 experience almost identical inputs relative to ground, and hence leakage currents are rejected.

Figure 5:
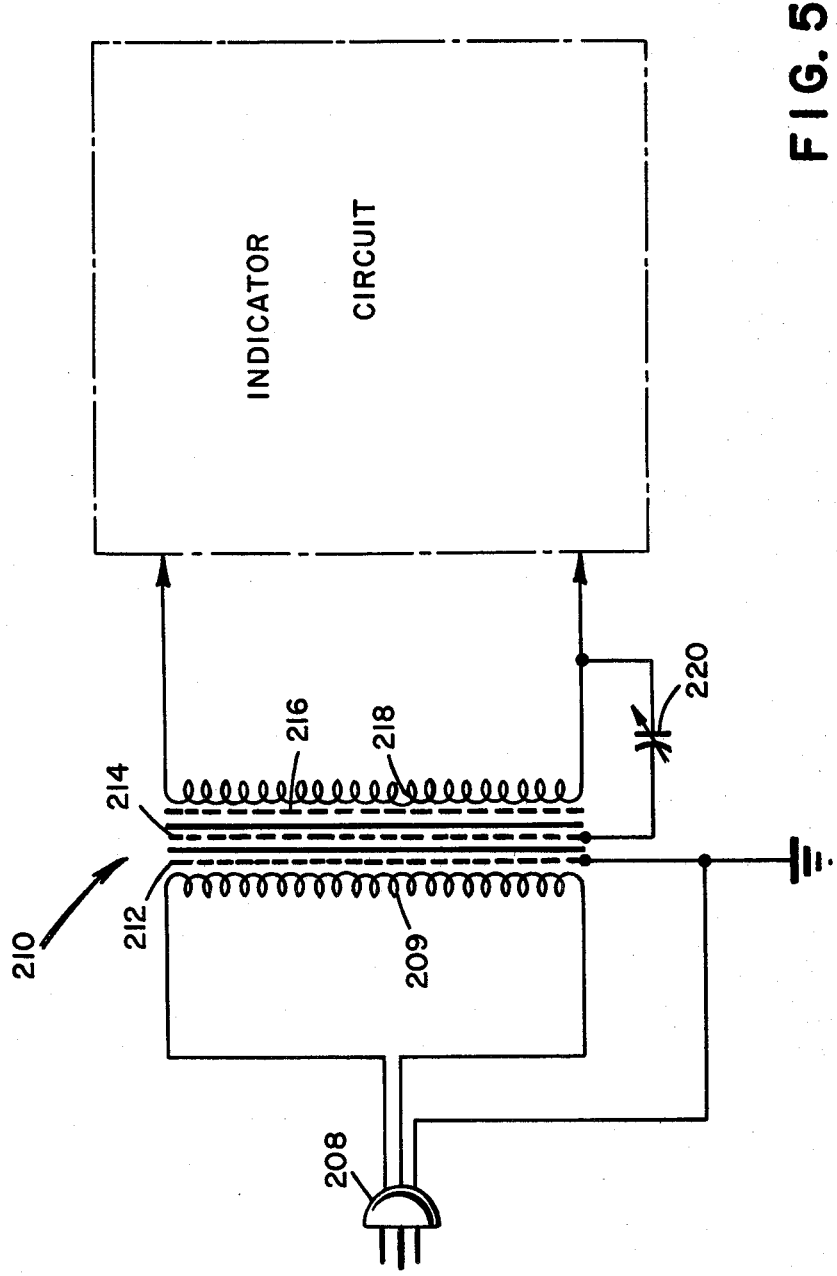
FIG. 5 is a schematic of still another circuit for minimizing leakage currents.

Turning now to FIG. 5, there is illustrated still another embodiment of an input circuit for minimizing leakage current. Here, power is derived through a male plug 208, adapted to associate with standard household current. The plug 208 feeds the primary winding 209 of an isolation transformer 210, preferably a one-to-one type transformer, and including three internal shields designated 212, 214 and 216. As is common, internal shield 212 is connected to the ground lead of male plug 208, and forms a common chassis ground. The secondary winding 218 of transformer 210 feeds power to a circuit such as that shown in FIG. 1 immediately to the right of input transformer 12. It may of course be necessary to step down the voltage across the secondary winding 218 of transformer 210, or to utilize transformer 210 as a low voltage transformer by employing a step-down stage immediately after the input from household current.

The third internal shield 214 of transformer 210 is connected to one side of the secondary winding 218 through a variable trimming capacitor 220. It is this trimming capacitor which results in low leakage current operation of the input circuit illustrated in FIG. 5. Capacitor 220 serves as cancel the inter-electrode capacitance between the windings of the transformer 210, and is adjusted to minimize leakage current. This FIG. 5 arrangement can replace transformer 12 of FIGS. 1 and 2 or the high input impedance circuit illustrated in FIG. 4.

Above, specific embodiments of the present invention have been described. It should be appreciated, however, that these embodiments were described for purposes of illustration only, without any intention of limiting the scope of the present invention. Rather, it is the intention that the present invention be limited not by the above but only as is defined in the appended claims.

What is claimed is:

1. An apparatus for indicating the end point quality of a liquid such as water wherein the liquid is generally non-conductive when of a high quality and becomes more conductive when its quality falls, the apparatus comprising: first and second conductive probe means spaced apart from one another, and adapted to reside within said liquid; excitation means for applying electrical energy across said first and second probe means; isolation means for electrically isolating said excitation means from said probe means; sensor means for sensing the conductivity of said liquid by monitoring current flow between said first and second probe means; means for developing an electrical indicator signal representative of the conductivity of said liquid; threshold means for developing an electrical threshold signal; comparator means for comparing said indicator signal to said threshold signal and for issuing one or the other of two output signals depending upon the magnitude of said indicator signal relative to said threshold signal; indicator means having two states, one of which indicates acceptable liquid quality, and the other of which indicates unacceptable liquid quality; and switch means responsive to the output signals issued by said comparator means for switching said indicator means between said two states depending upon the output signal issued by said comparator means.

2. The apparatus recited in claim 1, wherein said isolation means for isolating said excitation means from said probe means comprises a transformer and further comprising a bypass capacitor means connected from the secondary winding of said transformer to ground for bypassing any leakage current across said transformer to ground.

3. The apparatus recited in claim 1, wherein said indicator means is a lamp.

4. The apparatus recited in claim 1, wherein said switch means is an integrated circuit switch.

5. The apparatus recited in claim 1, and further comprising output switching means for controlling the operation of external loads, said output switching means being triggered by the state of said switch means.

6. The apparatus recited in claim 5, wherein said isolation means for isolating said excitation means from said probe means comprises a transformer.

7. The apparatus recited in claim 5, and further comprising a light emitting diode in series with said indicator means; a phototransistor electrically isolated from said light emitting diode, for receiving light emitted by said light emitting diode, and for becoming conductive upon receipt of said light; zero voltage switch means for sensing the state of said phototransistor, and for issuing gating signals upon said phototransistor being conductive; electrical receptacle means for associating with external load means and for delivering power thereto; power means for energizing said electrical receptacle means; gated triac switch means in the circuit between said electrical receptacle means and said power means; and means for delivering said gating signals to the gate of said triac switch means.

8. The apparatus recited in claim 1, wherein said comparator means is an operational amplifier having a non-inverting input and an inverting input; wherein said indicator signal is impressed upon one of said inputs; and wherein said threshold signal is impressed upon the other of said inputs.

9. The apparatus recited in claim 8, wherein said switch means is a transistor switch; wherein said transistor switch is biased by the output signal of said operational amplifier; and wherein said operational amplifier changes state at the threshold wherein said indicator signal is of the same magnitude as said threshold signal.

10. The apparatus recited in claim 9, wherein said indicator means and said transistor switch form a series circuit with the secondary winding of a power transformer, and wherein the state of said transistor switch opens and closes said series circuit.

11. The apparatus recited in claim 8, wherein the electrical energy applied across said first and second probe means is an A.C. signal on the order of 12 volts.

12. The apparatus recited in claim 1, wherein said first and second probe means and said indicator means are encapsulated in a casing of plastic material; wherein said sensor means, said means for developing the indicator signal, said comparator means and said switch means are located in a housing remote from said casing, and connected thereto by means of electrical cable; and wherein said excitation means is delivered to said housing by means of electrical cable.

13. The apparatus recited in claim 12, and further comprising output switching means for controlling the operation of external loads, said output switching means being triggered by the state of said switch means.

14. The apparatus recited in claim 13, wherein said output switching means is located within said housing.

15. The apparatus recited in claim 8, wherein said casing is threaded to associate with the discharge spout of a demineralizer unit.

16. An end point quality light for use with a water demineralizer unit to indicate the end point quality of the water discharged from said demineralizer unit, said end point quality light comprising: first and second conductive probes, speced apart from one another, and adapted to contact the water being discharged from the demineralizer unit; an indicator lamp for indicating acceptable or unacceptable water quality; a casing for encapsulating said probes and said indicator lamp, and including mounting means for supporting said casing on said demineralizer unit; excitation means for applying electrical energy to said probes; means for sensing the conductivity of the water by monitoring the current flowing between said probes; isolation means for electrically isolating said excitation means from said probe means; means for developing an indicator signal representative of the sensed conductivity; means for developing a threshold signal; comparator means for comparing said indicator signal with said threshold signal, and for issuing a control output signal when the conductivity of the water is below a predetermined conductivity represented by said threshold signal; switch means for responding to said control output signal by closing a circuit including said indicator lamp so as to illuminate said indicator lamp.

17. Apparatus for use with a liquid treatment unit comprising the combination of: an end point quality monitoring device including first and second conductive probes adapted to contact a liquid for monitoring the conductivity and hence the quality thereof, and an indicator lamp responsive to the conductivity of the liquid for indicating acceptable or unacceptable liquid quality; and output switching means for controlling the operation of external loads, the state of said output switching means being dependent upon whether the liquid quality is acceptable or unacceptable.

18. An end point quality monitoring device for use with a liquid treatment unit, said end point quality monitoring device comprising: first and second conductive probes adapted to contact the liquid for monitoring the conductivity and hence the quality thereof; sensor means for sensing the conductivity of said liquid by monitoring current flow between said first and second conductive probes; means for developing an electrical indicator signal proportional to the conductivity of said liquid; threshold means for developing an electrical threshold signal; comparator means for comparing said indicator signal with said threshold signal and for issuing an output signal whenever said indicator signal exceeds said threshold signal; and output switching means, the state of which is controlled by said output signal, for controlling external loads.

19. An apparatus for indicating the end point quality of a liquid such as water, wherein the liquid is generally non-conductive when of a high quality and becomes more conductive when its quality falls, the apparatus comprising: first and second probe means spaced apart from one another and adapted to reside within said liquid; excitation means for applying electrical energy across said first and second probe means; sensor means for sensing the conductivity of said liquid by monitoring current flow between said first and second probe means; indicator means having two states, one of which indicates acceptable liquid quality and the other of which indicates unacceptable liquid quality; switch means responsive to the current flow between said first and second probe means for switching said indicator means between said two states; and isolation transformer means having a high insulation breakdown point, the primary winding of which is adapted to associate with standard household 110-120v A.C. energization, and the secondary winding of which serves as said excitation means for electrically isolating the probe means from the standard household energization.

20. The apparatus recited in claim 19, wherein said excitation means applies on the order of 24 volts across said first and second probe means.

21. The apparatus recited in claim 19, and further comprising bypass capacitor means connected between one side of said secondary winding and ground.

22. The apparatus recited in claim 21, wherein said bypass capacitor has a value of between 10 and 160 mfd.

23. The apparatus recited in claim 22, wherein said bypass capacitor has a value of between 25 and 47 mfd.

24. An apparatus for indicating the end point quality of a liquid whose conductivity changes in dependence upon its quality, the apparatus comprising: first and second conductive probe means spaced apart from one another and adapted to reside within said liquid; excitation means for applying electrical energy across said first and second probe means; sensor means for sensing the conductivity of said liquid by monitoring current flow between said first and second probe means; means for developing an electrical indicator signal representative of the conductivity of said liquid; indicator means having two states, one of which indicates acceptable liquid quality and the other of which indicates unacceptable liquid quality; and switch means responsive to said indicator signal for switching said indicator means between said two states.

25. The apparatus recited in claim 24, wherein said excitation means is a transformer, the primary winding of which associates with standard household 110-120v A.C. energization, and the secondary winding of which applies electrical energy across said first and second probe means.

26. The apparatus recited in claim 25, and further comprising capacitor means connected between one side of said secondary winding and ground, for bypassing leakage current across said transformer to ground.

27. The apparatus recited in claim 25, wherein said transformer is internally shielded; and further comprising trimming capacitor means connected between transformer shielding and one side of the secondary winding.

28. The apparatus recited in claim 27, wherein said transformer is of the one-to-one isolation type.

29. The apparatus recited in claim 27, wherein said trimming capacitor means is of a value between 1.5 and 7.0pf.

30. For use in indicating the end point quality of a liquid, the combination comprising: sensor means for monitoring the quality of the liquid; end point indicator means having two states, one of which indicates acceptable liquid quality, and the other of which indicates unacceptable liquid quality; means for switching said end point indicator means in dependence upon the quality of the liquid sensed by said sensor means; auxiliary equipment adapted to be controlled in dependence upon the quality of the liquid; and control means for controlling the state of said auxiliary equipment means in dependence upon the quality of the liquid sensed by said sensor means.

31. An end point quality monitoring device for monitoring the quality of a liquid whose conductivity is inversely proportional to quality, the device comprising: first and second conductive probes adapted to contact a liquid, for monitoring the conductivity and hence the quality thereof; sensor means for sensing the conductivity of said liquid by monitoring current flow between said first and second conductive probes; means for developing an electrical indicator signal proportional to the conductivity of said liquid; threshold means for developing an electrical threshold signal; high input impedance isolation amplifier means for receiving said indicator signal and said threshold signal and for issuing first and second output signals proportional to said indicator signal and said threshold signal, repectively; comparator means for comparing the values of the respective outputs of said isolation means, and for issuing a control signal whenever said indicator signal exceeds said threshold signal; and indicator means for reacting to said control signal for indicating acceptable or unacceptable liquid quality.

32. The device recited in claim 31, wherein said isolation amplifier means comprises first and second amplifiers operated in unity, or buffer, configuration.

* * * * *